US00PP30868P2

(12) United States Plant Patent
Hansen

(10) Patent No.: US PP30,868 P2
(45) Date of Patent: Sep. 3, 2019

(54) ***BUDDLEIA* PLANT NAMED 'GRAND CASCADE'**

(50) Latin Name: *Buddleia davidii*
Varietal Denomination: Grand Cascade

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 15/932,773

(22) Filed: Apr. 23, 2018

(51) Int. Cl.
*A01H 5/02* (2018.01)

(52) U.S. Cl.
USPC ..... Plt./242

(58) Field of Classification Search
USPC ..... Plt./242

CPC ... A01H 5/02; A01H 5/00; A01H 5/08; A01H 5/0812; A01H 6/30; A01H 6/00
See application file for complete search history.

(56) References Cited

PUBLICATIONS

Roccommunity Plants That Cascade &LY53 2014, retrieved on Apr. 3, 2019, retrieved from the Internet at https://roccommunitysummit.org/plants-that-cascade-ly53.hta, pp. 1,20,37-41. (Year: 2014).*

* cited by examiner

*Primary Examiner* — June Hwu

(57) ABSTRACT

The new and distinct plant of *Buddleia* 'Grand Cascade' is a rounded-mounded, multi-stemmed, winter-hardy butterfly bush with very long, slightly drooping, flowering thyrse producing a cascading effect over a long season beginning mid-summer with sweetly-fragrant flowers of strong purple petals that are attractively offset by dark green foliage with silvery undersides. The new plant is valuable for landscaping en masse, as an accent or as a potted specimen.

1 Drawing Sheet

Botanical classification: *Buddleia davidii.*
Variety denomination: 'Grand Cascade'.

BACKGROUND OF THE PLANT

The present invention relates to the new and distinct butterfly bush plant of the Scrophulariaceae family, *Buddleia* 'Grand Cascade' developed by Hans A. Hansen in the fall of 2013 at a wholesale perennial nursery in Zeeland, Mich., USA. 'Grand Cascade' is the result of an ongoing breeding program conducted by the inventor. The goals for this program have been to produce improved, garden-worthy plants for the ornamental plant market. The new plant, was assigned the breeder code 13-8-2 toward the end of the evaluation trials. It is a single seedling selection from a cross-pollination between the unreleased proprietary hybrid 11-34-03 (not patented) as the female or seed parent. The male parent was 'Wisteria Lane' U.S. Plant Pat. No. 27,833. The new cultivar was discovered and selected as single individual flowering plant within the progeny of the above stated controlled-pollination during the summer 2015 in a controlled environment at the same nursery in Zeeland, Mich.

No plants of *Buddleia* 'Grand Cascade' have been sold, under this or any other name, in this country or anywhere in the world, prior to the filing of this application, nor has any disclosure of the new plant been made prior to the filing of this application with the exception of that which may have been sold or disclosed within one year of the filing date of this application and was either derived directly or indirectly from the inventor.

*Buddleia* 'Grand Cascade' was first asexually propagated from a single select plant in 2015 by stem cuttings at the same nursery in Zeeland, Mich. The resultant asexually propagated plants have been found to be stable and true to type in successive generations of asexual reproduction.

SUMMARY OF THE INVENTION

Plants of the new *Buddleia* have not been observed under all possible environmental conditions. The phenotype may vary somewhat with variations in environment and cultural practices such as temperature, light intensity, available moisture and fertility without, however, any variance in genotype.

In comparison to the new plant the female parent has lavender flowers that are more upright and the plant habit is less arching.

The nearest comparison plants known to the inventor are *Buddleia* 'Lavender Cupcake' U.S. Plant Pat. No. 28,221, 'Wisteria Lane' U.S. Plant Pat. No. 27,833, 'Butterfly Heaven' U.S. Plant Pat. No. 19,935 and the two co-pending applications from the same inventor 'Lavender Cascade' U.S. Plant patent application Ser. No. 15/932,774 and 'Pink Cascade' U.S. Plant patent application Ser. No. 15/932,743. 'Lavender Cupcake' is a smaller plant in habit and thyrse size with different colored flowers. 'Wisteria Lane' is shorter in habit with smaller thyrse and the branches are more drooping instead of mainly the thyrse drooping with light purple flowers. 'Butterfly Heaven' is shorter and narrower in habit, with less drooping of the thyrse, the thyrse is shorter and narrower and flower color is light violet 'Lavender Cascade' has slightly shorter and narrower thyrse. 'Pink Cascade' has slightly shorter and narrower thyrse, and the flower petal color is a medium pink.

*Buddleia* 'Grand Cascade' is a unique winter-hardy butterfly bush different from all other *Buddleia* cultivars known to the inventor based on the following combined repeatedly observed distinguishing traits:

1. Winter-hardy butterfly bush shrub, with multiple-stemmed, well-branched, rounded, waterfall-type mounded habit.
2. Huge, broad, many-flowered, elongated and slightly-drooping thyrse flowering over a prolonged season beginning mid-summer.
3. Flowers with strong purple petals.
4. Lanceolate foliage of dark green with silvery undersides.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
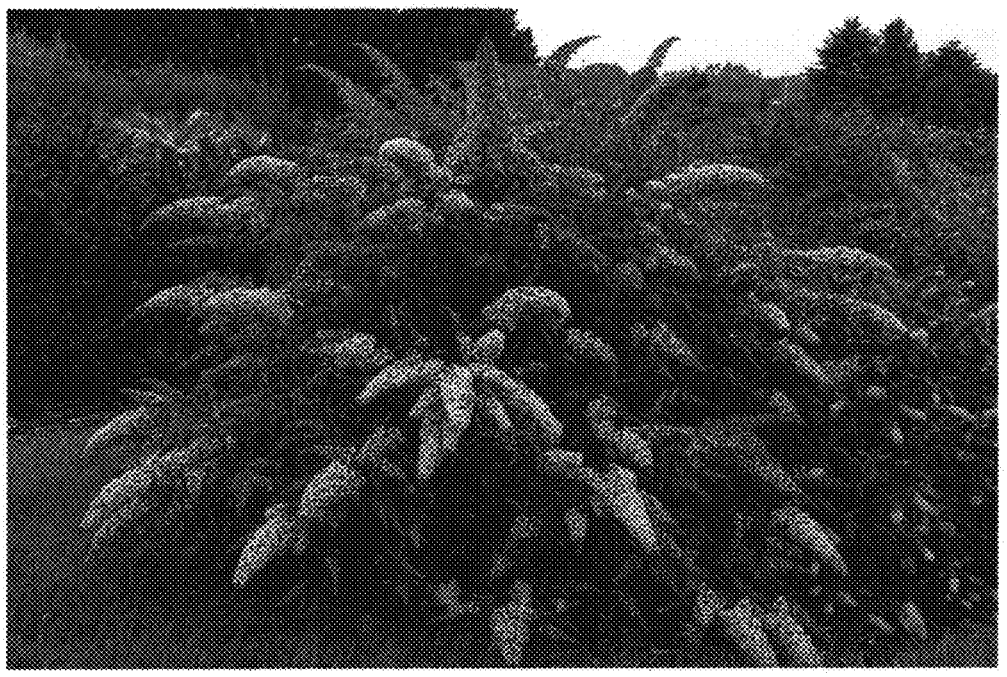
FIG. 1 shows the habit of a four-year-old plant in mid-season flowering.
Figure 2:
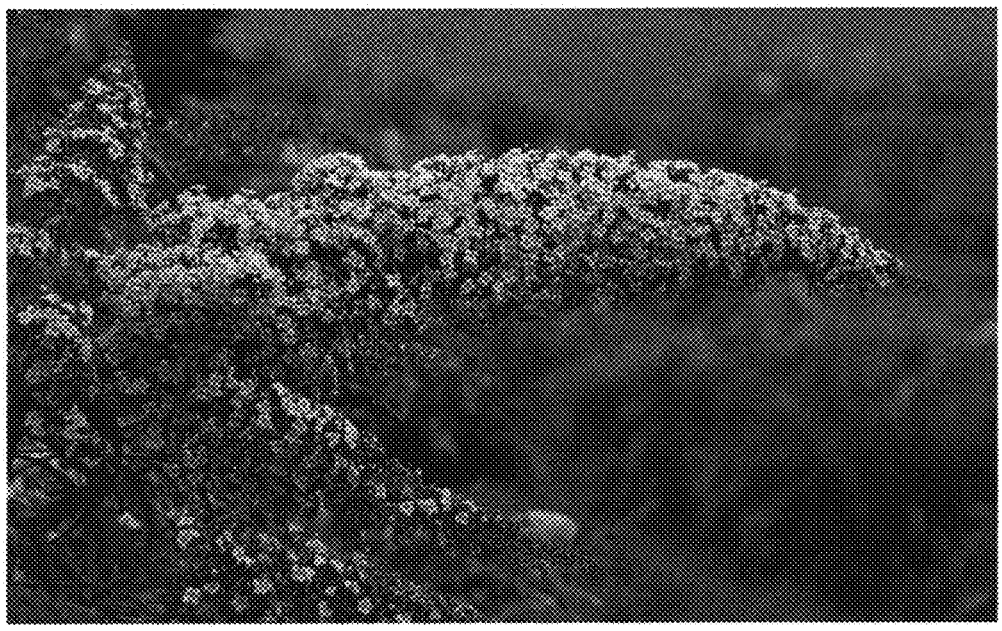
FIG. 2 shows a close-up of the inflorescence.

The following descriptions and color references are based on the 2015 edition of The Royal Horticultural Society Colour Chart except where common dictionary terms are used. The new plant, *Buddleia* 'Grand Cascade', has not been observed under all possible environments. The phenotype may vary slightly with different environmental conditions, such as temperature, light, fertility, moisture and maturity levels, but without any change in the genotype. The following observations and size descriptions are of four-year-old plants in the loamy-sand, open-sun, field trials of a nursery in Zeeland, Mich. with supplemental fertilizer and water as needed. The plants are natural habit and were not treated with plant growth regulators, nor were they pinched at any time in the growth year except to cut back woody stems to about 15 cm tall in early spring.

Parentage: Unreleased proprietary hybrid 11-34-03 (not patented) as the female or seed patent; the male or pollen parent was 'Wisteria Lane';

Propagation:

*Method*.—Softwood shoot cuttings.

*Time to initiate roots from tissue culture*.—About two weeks.

*Rooting habit*.—Normal, dense and branching, developing thick at base to about 1.5 cm diameter.

*Root color*.—Creamy white between RHS 159A and lighter than RHS 159 D depending on soil type.

*Crop time*.—Under normal summer growing conditions 12 to 15 weeks to flower in a four-liter container from cutting. Plant vigor is very good.

Plant description:

*Plant shape and habit*.—Winter-hardy, herbaceous to semi-woody, well-branched shrub with about 32 thick upright and branched main stems producing a rounded mound, to about 180 cm tall and about 270 cm wide.

*Stem*.—Terete and woody in lower portion, with exfoliating bark; younger upper portion tomentose to tomentulose; strong and flexible, drooping with flower and bud production; average about 135 cm tall from soil line to just below terminal flowers, and about 15.0 mm diameter at the base; about 24 branches per main stem before distal flowers in upper 12 nodes, extending at about 45° angle from main stem.

*Stem color*.—Young distal portion just below flowers between RHS 192B and RHS 192C; basal 15 cm between RHS 200C and RHS 165B with striations between RHS 200A and RHS N199B.

*Internode*.—About 18 nodes per main stem below terminal thyrse, average internode length about 7.5 cm on unpinched plant; upper internodes slightly more elongated than lower internodes.

Foliage description: Opposite; lanceolate; decussate; serrate with about three teeth per cm, teeth about 1.0 mm long and 3.0 mm wide; young expanding leaves puberulent abaxial and adaxial, becoming glabrous adaxial; attenuate to cuneate base and acute apex; sessile; no foliar fragrance detected;

*Leaf blade size*.—Up to about 16.0 cm long and about 3.0 cm wide, average about 8.5 cm long and about 22.0 mm wide; becoming smaller in distal portion of stem.

*Foliage color*.—Young expanding leaf adaxial blend between RHS 189C and RHS 138B, young expanding abaxial nearest RHS N189C; mature leaves adaxial between RHS 137A and RHS NN137A, mature abaxial nearest RHS 193D.

*Veins*.—Reticulate; abaxial costate, puberulent; adaxial glabrous, slightly impressed.

*Vein color*.—Abaxial midrib nearest RHS 192D and secondary veins nearest RHS 193D; adaxial midrib nearest RHS NN137A and secondary veins RHS 137A and RHS NN137A.

*Petioles*.—Leaves sessile.

*Inflorescence description*.—Glomerate thyrse consisting of about 2,000 to 4,000 self-cleaning salverform flowers; to about 58.0 cm long and about 15.5 cm across, average about 41.0 cm long and 13.0 cm across; beginning in mid-July and continuing until frost in Michigan.

*Inflorescence attitude*.—Slightly drooping.

*Flower buds*.—Elongated clavate with long tube base, apex rounded; one day prior to opening about 13.0 mm long, about 2.5 mm diameter in club, tube about 1.0 mm diameter and about 8.0 mm long.

*Flower bud color*.—Nearest RHS N82C in club portion, basal one-third of tube portion nearest RHS 155D, distal two-thirds of tube nearest RHS 83C.

*Sepals*.—Typically four, proximal two-thirds connate, adpressed to corolla tube; acute apex; glabrous adaxial and pubescent abaxial; margin entire; fused in about the basal 1.7 mm and split in about the terminal 0.9 mm; forming a corolla about 2.6 mm long and about 1.0 mm across; individually less than about 1.0 mm wide at point of fusion.

*Sepal color*.—Adaxial and abaxial nearest RHS 138A along center longitudinal axis and nearest RHS 138D along margins of abaxial and adaxial.

*Flowers*.—Salverform; with straight terete tube about 9.0 mm long and 1.0 mm diameter, and a abruptly applanate face about 7.0 mm across; attitude outward from thyrse center.

*Flowers fragrance*.—Pleasantly and distinctly sweet.

*Petals*.—Typically four, rarely five; glabrous abaxial and on adaxial blades and tube, puberulent center abaxial tube; blade rounded with crenate margin; apex rounded; blade to about 2.5 mm across and about 3.0 mm long from fused face; corolla lobes free and not imbricate.

*Petal color*.—Upon opening and when fully open adaxial tube base nearest RHS 155D, distal one half tube center nearest RHS 85D, adaxial face blades nearest RHS 84A; upon opening and when fully open adaxial blade center and distal tube nearest RHS N25C, abaxial tube base nearest RHS 155D, distal two-thirds of tube nearest RHS 83C and abaxial petal blades between RHS 84B and RHS 84A.

*Gynoecium*.—Pistil: one; about 4.8 mm long. Style: short, round, glabrous; about 1.3 mm long and less than 0.2 mm diameter; color nearest RHS 145D. Stigma: narrow ellipsoidal, minutely puberulent; about 0.2 mm in diameter and about 1.5 mm long; color nearest RHS 144B. Ovary: superior; oblong globose; about 1.0 mm across at base and 2.0 mm tall; distally tapering to style; color nearest RHS 145A.

*Androecium*.—Typically four. Filaments: not produced or very short. Anthers: typically four; oblong; introrse; adnate to about mid-point of corolla tube; about 1.0 mm long and 0.5 mm wide; color nearest RHS 18D. Pollen: globose, less than 0.1 mm long; color nearest RHS 18D.

*Pedicel*.—Short, puberulent; about 1.0 mm long and about 0.5 mm diameter; color nearest RHS N138C.

*Peduncle*.—Quadrangular; tomentulose to tomentose, flexible and strong; to about 58.0 cm long total, and about 3.0 mm across at base below flowers.

*Peduncle color*.—Nearest RHS 192A.

*Fruit*.—Moderate to heavy fruit set; oblong with acute apex; attenuate base; glabrous, bi-valved, septicidal capsule; about 11.0 mm long and about 1.8 mm diameter toward apex and 1.0 mm toward base.

*Fruit color*.—As maturing nearest RHS 187A; when mature and dehiscing nearest RHS 164B.

*Seed*.—Elongated linear with sharply acute ends; about 1.5 mm long and less than 0.2 mm across in center.

*Seed color*.—Nearest RHS 200A.

Disease resistance: Resistance has been noted to deer browsing. Other pest and disease resistance beyond that common to butterfly bush cultivars has not been observed. The plant grows best with plenty of moisture and adequate drainage, but is able to tolerate some drought when mature.

Hardiness at least from USDA zone 6 through 10.

It is claimed:

1. A new cultivar of winter-hardy butterfly bush plant named *Buddleia* 'Grand Cascade' as herein illustrated and described.

* * * * *